(12) United States Patent
Lawrenson et al.

(10) Patent No.: US 10,284,817 B2
(45) Date of Patent: May 7, 2019

(54) DEVICE FOR AND METHOD OF CORNEAL IMAGING

(71) Applicant: Telefonaktiebolaget LM Ericsson (publ), Stockholm (SE)

(72) Inventors: Matthew John Lawrenson, Bussigny (CH); Julian Charles Nolan, Pully (CH)

(73) Assignee: Telefonaktiebolaget LM Ericsson (publ), Stockholm (SE)

( * ) Notice: Subject to any disclaimer, the term of this patent is extended or adjusted under 35 U.S.C. 154(b) by 44 days.

(21) Appl. No.: 15/496,274

(22) Filed: Apr. 25, 2017

(65) Prior Publication Data

US 2017/0230621 A1    Aug. 10, 2017

Related U.S. Application Data

(63) Continuation of application No. PCT/SE2014/051476, filed on Dec. 10, 2014.

(51) Int. Cl.
*H04N 7/18* (2006.01)
*A61B 3/00* (2006.01)
(Continued)

(52) U.S. Cl.
CPC ........... *H04N 7/181* (2013.01); *A61B 3/0025* (2013.01); *A61B 3/0041* (2013.01); *A61B 3/107* (2013.01);
(Continued)

(58) Field of Classification Search
CPC ..... H04N 7/181; G06F 3/0488; G06F 3/0412; G06F 1/1626; G06F 1/1643
(Continued)

(56) References Cited

U.S. PATENT DOCUMENTS

| 4,692,003 A * | 9/1987 | Adachi | A61B 3/107 351/212 |
| 5,418,714 A * | 5/1995 | Sarver | H04N 19/50 128/922 |

(Continued)

FOREIGN PATENT DOCUMENTS

| JP | H07248216 A | 9/1995 |
| WO | WO 2016/064311 A1 | 4/2016 |

OTHER PUBLICATIONS

Spoelder et al, A basic design for adaptive corneal topography (Year: 1999).*

(Continued)

*Primary Examiner* — Shan E Elahi
(74) *Attorney, Agent, or Firm* — Sage Patent Group

(57) ABSTRACT

A device for corneal imaging is disclosed. The device comprises a first camera and processing means. The first camera is configured for imaging a cornea of a user of the device and/or an eyewear worn by the user. The processing means is operative to acquire a first image from the first camera, identify a first reflection by the cornea and/or a second reflection by a reflective surface of the eyewear, and determine a first optical transformation representing the first reflection and/or a second optical transformation representing the second reflection. Embodiments of the invention provide an improved corneal imaging solution for user operated computing devices by taking specular reflections originating from one or more reflective surfaces of an eyewear worn by the user into consideration. Also disclosed are a corresponding method, computer program, and computer program product.

31 Claims, 5 Drawing Sheets

(51) Int. Cl.
*A61B 3/14* (2006.01)
*A61B 3/107* (2006.01)
*A61B 3/15* (2006.01)
*G02B 17/08* (2006.01)
*G06F 3/01* (2006.01)
*G06F 3/042* (2006.01)
*G06T 3/00* (2006.01)
*G06T 15/04* (2011.01)
*G06F 3/0488* (2013.01)
*G06F 1/16* (2006.01)
*G06F 3/041* (2006.01)
*G03B 15/14* (2006.01)

(52) U.S. Cl.
CPC ............... *A61B 3/14* (2013.01); *A61B 3/152* (2013.01); *G02B 17/08* (2013.01); *G06F 1/1626* (2013.01); *G06F 1/1643* (2013.01); *G06F 1/1686* (2013.01); *G06F 3/013* (2013.01); *G06F 3/0412* (2013.01); *G06F 3/0416* (2013.01); *G06F 3/0425* (2013.01); *G06F 3/0488* (2013.01); *G06T 3/0062* (2013.01); *G06T 15/04* (2013.01); *G03B 15/14* (2013.01); *G06F 2203/04106* (2013.01); *G06F 2203/04108* (2013.01)

(58) Field of Classification Search
USPC ........................................................ 348/78
See application file for complete search history.

(56) References Cited

U.S. PATENT DOCUMENTS

| | | | |
|---|---|---|---|
| 5,621,457 A | 4/1997 | Ishiwaka et al. | |
| 5,983,030 A | 11/1999 | Nagano | |
| 6,296,358 B1* | 10/2001 | Cornsweet | A61B 3/156 351/206 |
| 7,025,459 B2* | 4/2006 | Cornsweet | A61B 3/156 351/200 |
| 7,360,895 B2* | 4/2008 | Cornsweet | A61B 3/12 351/206 |
| 8,770,753 B2* | 7/2014 | Hee | A61B 3/0025 351/206 |
| 2003/0206272 A1* | 11/2003 | Cornsweet | A61B 3/156 351/206 |
| 2004/0059321 A1* | 3/2004 | Knopp | A61B 3/13 606/10 |
| 2004/0263784 A1* | 12/2004 | Cornsweet | A61B 3/12 351/221 |
| 2011/0085139 A1 | 4/2011 | Blixt et al. | |
| 2011/0299034 A1* | 12/2011 | Walsh | A61B 3/102 351/206 |
| 2012/0140174 A1* | 6/2012 | Hee | A61B 3/0025 351/206 |
| 2013/0002846 A1 | 1/2013 | De Bruijn et al. | |
| 2013/0296710 A1* | 11/2013 | Zuzak | A61B 5/0071 600/476 |
| 2013/0329186 A1* | 12/2013 | Contet | G02C 7/028 351/159.77 |
| 2014/0002349 A1* | 1/2014 | Hansen | A61B 3/113 345/156 |
| 2014/0062868 A1* | 3/2014 | Blixt | A61B 3/113 345/156 |

OTHER PUBLICATIONS

Office Action for Russian Application No. 2017122746 dated May 31, 2018 (11 pages).
Nishino et al., "Corneal Imaging System: Environment from Eyes", International Journal of Computer Vision, vol. 70, No. 1, pp. 23-40 (Oct. 2006).
Nishino et al., "Eyes for Relighting", ACM Transactions on Graphics (TOG)—Proceedings of ACM SIGGRAPH 2004, vol. 23, Issue 3, pp. 704-711 (Aug. 2004).
Nitschke et al., "Corneal Imaging Revisited: An Overview of Corneal Reflection Analysis and Applications", IPSJ Transactions on Computer Vision and Applications, vol. 5, pp. 1-18 (Jan. 2013).
Wu et al., "Eulerian Video Magnification for Revealing Subtle Changes in the World", ACM Transactions on Graphics (TOG)—Proceedings of ACM SIGGRAPH 2012, vol. 31, Issue 4, pp. 1-8 (Jul. 2012).
Notification of Transmittal of the International Search Report and the Written Opinion of the International Searching Authority, or the Declaration for International Application No. PCT/SE2014/051476, 12 pages (dated Aug. 7, 2015).
Takemura et al. "Estimating Focused Object using Corneal Surface Image for Eye-based Interaction", Retrieved from URL:http://2013.petmei.org/wp-content/uploads/2013/09/petmei2013_session3_3.pdf, pp. 1-5 (Sep. 25, 2013).
Written Opinion of the International Preliminary Examining Authority for International Application No. PCT/SE2014/051476, 7 pages (dated Oct. 26, 2016).
Ye et al., "Video Enhancement of People Wearing Polarized Glasses: Darkening Reversal and Reflection Reduction," 2013 IEEE Conference on Computer Vision and Pattern Recognition. Proceedings, IEEE Computer Society, US, pp. 1179-1186 (Jun. 23, 2013).
International Preliminary Report on Patentability for International Application No. PCT/SE2014/051476, 5 pages (dated Feb. 23, 2017).

* cited by examiner

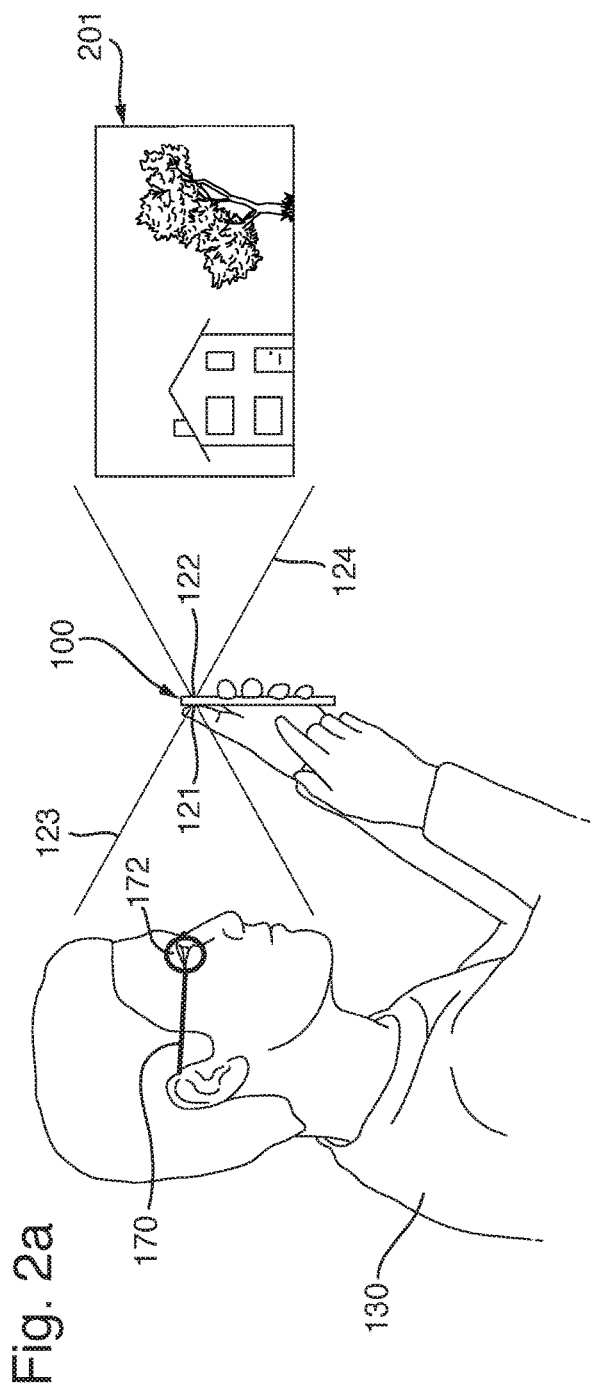
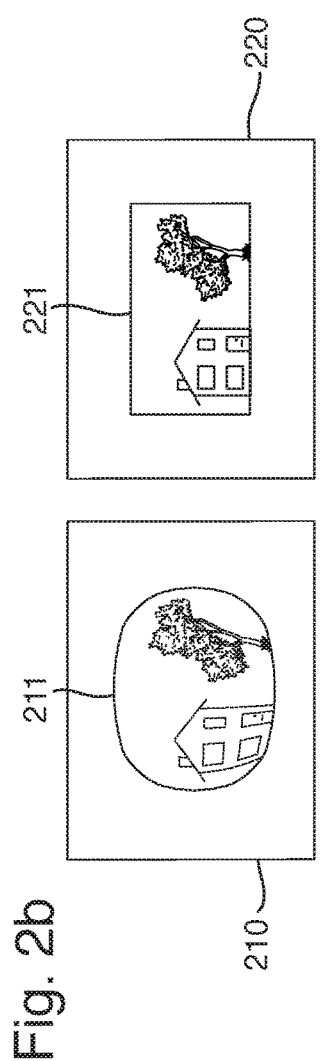

DEVICE FOR AND METHOD OF CORNEAL IMAGING

CROSS REFERENCE TO RELATED APPLICATION

This application is a continuation of PCT International Application No. PCT/SE2014/051476, filed on 10 Dec. 2014, the disclosure and content of which is incorporated by reference herein in its entirety.

TECHNICAL FIELD

The invention relates to a device for corneal imaging, a method of corneal imaging performed by a device, a corresponding computer program, and a corresponding computer program product.

BACKGROUND

The use of corneal imaging with hand-held and other devices such as mobile phones, smartphones, tablets, laptops, and the like, requires that a corneal imaging based interface must work reliably across a range of different operating conditions, including when eyewear such as glasses, spectacles, sunglasses, goggles, or a contact lenses, is worn by a user operating the device.

Corneal imaging is a technique which utilizes a camera for imaging a person's cornea, in particular that of the user of the device, for gathering information about what is in front of the person and also, owing to the spherical nature of the human eyeball, for gathering information about objects in a field-of-view which is wider than the person's viewing field-of-view. Such objects may potentially be outside the camera's field-of-view and even be located behind the camera. The technique is made possible due to the highly reflective nature of the human cornea, and also the availability of high-definition cameras in devices such as smartphones and tablets. An analysis of the characteristics of the corneal imaging system has been given by K. Nishino and S. K. Nayar, "Eyes for relighting", in ACM SIGGRAPH 2004 Papers (SIGGRAPH '04), ACM, New York, 2004, pages 704-711.

Glasses may be worn to correct vision, for fashion, to avoid glare, or for protection, and are manufactured with a range of surface finishes that range from those which seek to avoid surface reflections to highly reflective coatings, and with various curvatures of lenses.

The use of eyewear, in particular such as prescription glasses or sunglasses, is likely to generate additional specular reflections originating from both the cornea of the user's eye and the glasses, or in the case of glasses with a highly reflective finish from the glasses alone. This may result in a corneal imaging system delivering erroneous results.

SUMMARY

It is an object of the invention to provide an improved alternative to the above techniques and prior art.

More specifically, it is an object of the invention to provide an improved corneal imaging solution for computing devices, and in particular hand-held devices, such as mobile phones, smartphones, tablets, laptops, and the like.

These and other objects of the invention are achieved by means of different aspects of the invention, as defined by the independent claims. Embodiments of the invention are characterized by the dependent claims.

According to a first aspect of the invention, a device for corneal imaging is provided. The device comprises a first camera and processing means. The first camera is configured for imaging a cornea of a user of the device, an eyewear worn by the user, or both. The processing means is operative to acquire a first image from the first camera, to identify a first reflection by the cornea and/or a second reflection by a reflective surface of the eyewear, and to determine a first optical transformation representing the first reflection and/or a second optical transformation representing the second reflection. The processing means is operative to identify the first reflection and/or the second reflection by analyzing the first image, i.e., by means of image processing.

According to a second aspect of the invention, a method of corneal imaging is provided. The method is performed by a device and comprises acquiring a first image from a first camera. The first camera is configured for imaging a cornea of a user of the device, an eyewear worn by the user, or both. The method further comprises identifying a first reflection by the cornea and/or a second reflection by a reflective surface of the eyewear, and determining a first optical transformation representing the first reflection and/or a second optical transformation representing the second reflection. The first reflection and/or the second reflection are identified by analyzing the first image, i.e., by means of image processing.

According to a third aspect of the invention, a computer program is provided. The computer program comprises computer-executable instructions for causing a device to perform the method according to an embodiment of the second aspect of the invention, when the computer-executable instructions are executed on a processing unit comprised in the device.

According to a fourth aspect of the invention, a computer program product is provided. The computer program product comprises a computer-readable storage medium which has the computer program according to the third aspect of the invention embodied therein.

The invention makes use of an understanding that an improved corneal imaging solution for user operated computing devices, in particular hand-held devices, such as mobile phones, smartphones, tablets, laptops, and the like, may be achieved by taking specular reflections by eyewear worn by the user into consideration. Such reflections may originate from one or more reflective surfaces of an eyewear, e.g., a surface of a lens of glasses. A specular reflection is a mirror-like reflection of light from such a reflective surface. In some cases, if the eyewear is provided with a highly reflecting surface coating, such as certain types of sunglasses, the reflection from the eyewear may be the only reflection which is detected by the corneal imaging interface, the reflection by the cornea being obscured by the reflection from the eyewear and the darkened glasses.

In general, eyewear consists of items and accessories worn on or over the eyes of the user, for fashion or adornment, protection against the environment, or to improve or enhance visual acuity. Common forms of eyewear include glasses, also called eyeglasses or spectacles, sunglasses, and contact lenses, but may also include other forms of eye protection, such as goggles.

Known corneal imaging systems do not identify reflections caused by eyewear worn by the user and are unable to correct for the resulting multiple specular reflections from both the user's cornea and the eyewear, resulting in erroneous results.

The present disclosure provides a solution whereby additional reflective surfaces which are introduced between the cornea of the user and the imaging device, e.g., a smartphone which is provided with a front-facing camera configured for imaging a cornea of a user of the device and/or an eyewear worn by the user, are identified and characterized such that specular reflective images from either the cornea and/or glasses may be used either independently or together.

By identifying one or more reflections in the first image captured by the first camera, such as a front-facing camera which the device is provided with, optical transformations which represent reflection off the user's cornea or an eyewear worn by the user can be derived. Throughout this disclosure, a reflection from the cornea of an eye of the user is referred to as the first reflection, whereas a reflection originating from a reflective surface of an eyewear is referred to as the second reflection. It will be appreciated that some types of eyewear, in particular glasses with thick lenses, may give rise to more than one reflection, but it will for simplicity be assumed in the following that only one of these reflections is prominent in the first image. Embodiments of the invention which take multiple reflections from eyewear into consideration may easily be envisaged.

In the present context, an optical transformation is a transformation which transforms an image of an object of a scene within the field-of-view of the cornea, or that of the eyewear, into a reflection which is captured by the first camera. Due to the non-planar geometry of reflective surfaces of the human cornea as well as common forms of eyewear, the reflected image is distorted to an extent which is governed by the curvature of the reflecting surface.

For each of the identified reflections, the optical transformation describing the reflection may be derived based on a number of alternatives, as is elucidated further below. The derived optical transformations may subsequently be used for correcting corneal images, or for correction information extracted from corneal images, e.g., geometrical information pertaining to a scene captured in a corneal image. Throughout this disclosure, the notion of corneal imaging is to be understood to include images which capture reflections not only from the user's cornea but also from an eyewear worn by the user.

As an alternative to, or in addition to, deriving one or more optical transformations representing reflection from the user's cornea or eyewear worn by the user, embodiments of the invention may derive a geometrical model of the reflecting surface causing a reflection. For the adult human cornea, e.g., the geometry of its reflecting surface may be approximated by an ellipsoid with parameters which do not vary much across people. The situation is, however, different for eyewear, which is manufactured with varying curvatures of reflecting surfaces such as lenses.

Embodiments of the invention are advantageous in that they work more reliable than conventional devices based on corneal imaging which do not take additional reflections by eyewear worn by the user into account.

According to an embodiment of the invention, information describing the first optical transformation and/or the second optical transformation is determined. The information describing the first optical transformation and/or the second optical transformation may, e.g., comprise a first curvature of the cornea and/or a second curvature of a reflective surface of the eyewear. For an arbitrary reflecting surface, the curvature is in general a non-scalar quantity which may, e.g., be represented by various parameters such as a scalar curvature, or radius, and an eccentricity. Alternatively, the information may, e.g., be a suitable mathematical description of the first and/or the second optical transformation and may be based on one or more geometrical parameters or one or more matrices. Determining the information describing the first optical transformation and/or the second optical transformation is advantageous in that it subsequently may be used for correcting corneal images, or information extracted from corneal images, e.g., geometrical information pertaining to a scene captured in a corneal image. Optionally, the information may be provided to an application being executed on the device, such as an application utilizing corneal imaging.

According to an embodiment of the invention, the first optical transformation is a universal optical transformation representing reflection by the human cornea. That is, rather than determining the first optical transformation based on image analysis, it can be derived from the known geometry of the human cornea which, at least for adults, does not very much across people. Advantageously, the determined first optical transformation may be used in determining the second optical transformation, as is described herein.

According to an embodiment of the invention, the information describing the second optical transformation is retrieved from a database based on an identification, such as make and model, of the eyewear. Advantageously, the information describing the second optical transformation is acquired from a database which may be provided with the device or external to the device. In the latter case, the device may query the database via a communications network, e.g., a radio access network and/or the Internet. Alternatively, rather than retrieving the information describing the second optical transformation, one may also envisage embodiments retrieving the second optical transformation or a geometrical model of a reflective surface of the eyewear. Advantageously, the determined second optical transformation may be used in determining the first optical transformation, as is described herein.

According to another embodiment of the invention, the first optical transformation and/or the second optical transformation may be determined by identifying a reflection of the device in the first reflection and/or the second reflection, and determining the first optical transformation and/or the second optical transformation based on a shape of the device. This embodiment allows determining either of the first and the second optical transformation separately based on the shape of the device. This is achieved by identifying a reflection of the device in the first image, either the first reflection from the cornea or the second reflection from the eyewear, and deriving the first or the second optical transformation as the optical transformation which transforms the known shape of the device, typically close to a rectangle of known dimensions, into the distorted shape of the captured reflection of the device. Optionally, the device may further comprise a screen operable as output device for the device, and the reflection of the device is a reflection of the screen. Typically, the screen is provided on the same face as the first camera. Determining the first and/or the second optical transformation based on a reflection of the screen is advantageous in that reflections of the screen are prominent and easy to identify.

According to an embodiment of the invention, the first optical transformation and/or the second optical transformation are determined by determining one of the first optical transformation and the second optical transformation, identifying at least one object which is visible in both the first reflection and the second reflection, determining a third optical transformation between the at least one object in the first reflection and the at least one object in the second reflection, and determining the other optical transformation of the first optical transformation and the second optical transformation based on the determined optical transformation and the third optical transformation. This embodiment is advantageous if an object of a scene is captured in both reflections, i.e., in the first reflection and the second reflection. It is based on the understanding that, if one of the first optical transformation or the second optical transformation is known, or can be determined by one of the alternatives disclosed herein, the other optical transformation which is yet to be determined can be determined based on an optical transformation which transforms the object as captured in the first reflection into the object as captured in the second reflection, or vice versa. This solution can advantageously be used if both the first reflection and the second reflection are prominent in the captured first image and can be separated, such that an optical transformation, referred to as third optical reflection, between the object in the first reflection and the object in the second reflection can be derived. It will be appreciated that the third optical transformation does not represent reflection from a real reflective surface but is a means of describing and quantifying the difference in reflection off the cornea and the eyewear.

According to an embodiment of the invention, the device further comprises a second camera which has a field-of-view which is substantially opposite to a field-of-view of the first camera. Such camera is typically provided on a face of the device which is opposite to the face which includes the screen, and is frequently referred to as rear-facing camera. The first optical transformation and/or the second optical transformation are determined by acquiring a second image from the second camera, identifying at least one object which is present in both the first image and the second image, determining a fourth optical transformation between the at least one object in the first image and the at least one object in the second image, and determining the first optical transformation and/or the second optical transformation based on the fourth optical transformation. This embodiment is based on the understanding that a second image captured by a rear-facing camera does not suffer from distortions due to reflection from the cornea or the eyewear. Accordingly, by establishing an optical transformation, herein referred to as the fourth optical transformation, between an object captured in the first image and the same object as captured in the second image, the first or the second optical transformation may be determined. This embodiment is advantageous in situations when the device is aligned so as to capture the same object by the first camera, via reflection by the cornea and/or the eyewear, and by the second camera in a direct fashion, i.e., without involving reflection.

According to an embodiment of the invention, an image of the first reflection, an image of the second reflection, or both, is/are provided. That is, rather than providing information describing the first and/or the second optical transformation to an application being executed on the device, for using that information for corneal imaging purposes, images of the first and/or the second reflection may alternatively, or additionally, be provided to the application. Optionally, the image of the first reflection and/or the image of the second reflection may be corrected based on the first optical transformation and/or the second optical transformation, respectively, so as to reverse the distortion imposed by reflection from a non-planar surface, such as the cornea or the eyewear.

According to an embodiment of the invention, a combined image of the first reflection and of the second reflection is provided. That is, rather than providing only one image or two separate images of the first reflection and the second reflection, an image which is a combination of a corrected image of the first reflection and a corrected image of the second reflection is provided. Correcting an image is to be understood as performing an optical transformation which is the inverse of the first optical transformation or the second optical transformation, thereby reversing the distortion imposed by reflection off a non-planar surface. This is advantageous in that an image of improved quality may be obtained.

According to an embodiment of the invention, one or more metrics associated with requirements on an image of a reflection are determined for each of the image of the first reflection and the image of the second reflection, and the provided image is selected based on the determined one or more metrics. These metrics may, e.g., relate to any one, or a combination of, image quality, image resolution, visibility or presence of a certain object, such as a screen of the device, and so forth. Advantageously, based on the determined metric, one of the images of the first and the second reflection may be selected for subsequent use by a corneal imaging application. Thereby, the application is provided with an image of sufficient quality, resolution, capturing a certain object, or the like.

According to an embodiment of the invention, the device further comprises a screen operable as output device for the device, and graphical content is displayed on the screen so as to make the user move the device in relation to a head of the user. Under certain circumstances the first image, and maybe also the second image, may be of inferior quality or may not capture a desired object, i.e., an object which needs to be captured for the purpose of performing corneal imaging. For instance, the user may hold the device such that the reflection of a desired object, e.g., the screen, is not captured by the first camera. By displaying content on the screen so as to trigger the user to move his/her head and/or the device, an orientation of the device with respect to the user's head may be achieved which allows capturing images with improved properties. This may, e.g., be achieved by displaying blurred graphical content, or decreasing the size of the displayed graphical content, e.g., text, so as to trigger the user to move the device closer to his/her eyes.

Even though advantages of the invention have in some cases been described with reference to embodiments of the first aspect of the invention, corresponding reasoning applies to embodiments of other aspects of the invention.

Further objectives of, features of, and advantages with, the invention will become apparent when studying the following detailed disclosure, the drawings and the appended claims. Those skilled in the art realize that different features of the invention can be combined to create embodiments other than those described in the following.

BRIEF DESCRIPTION OF THE DRAWINGS

The above, as well as additional objects, features and advantages of the invention, will be better understood through the following illustrative and non-limiting detailed description of embodiments of the invention, with reference to the appended drawings, in which:

FIGS. 2a and 2b illustrate a device for corneal imaging, in accordance with another embodiment of the invention.

All the figures are schematic, not necessarily to scale, and generally only show parts which are necessary in order to elucidate the invention, wherein other parts may be omitted or merely suggested.

DETAILED DESCRIPTION

The invention will now be described more fully hereinafter with reference to the accompanying drawings, in which certain embodiments of the invention are shown. This invention may, however, be embodied in many different forms and should not be construed as limited to the embodiments set forth herein. Rather, these embodiments are provided by way of example so that this disclosure will be thorough and complete, and will fully convey the scope of the invention to those skilled in the art.

Figure 1A:
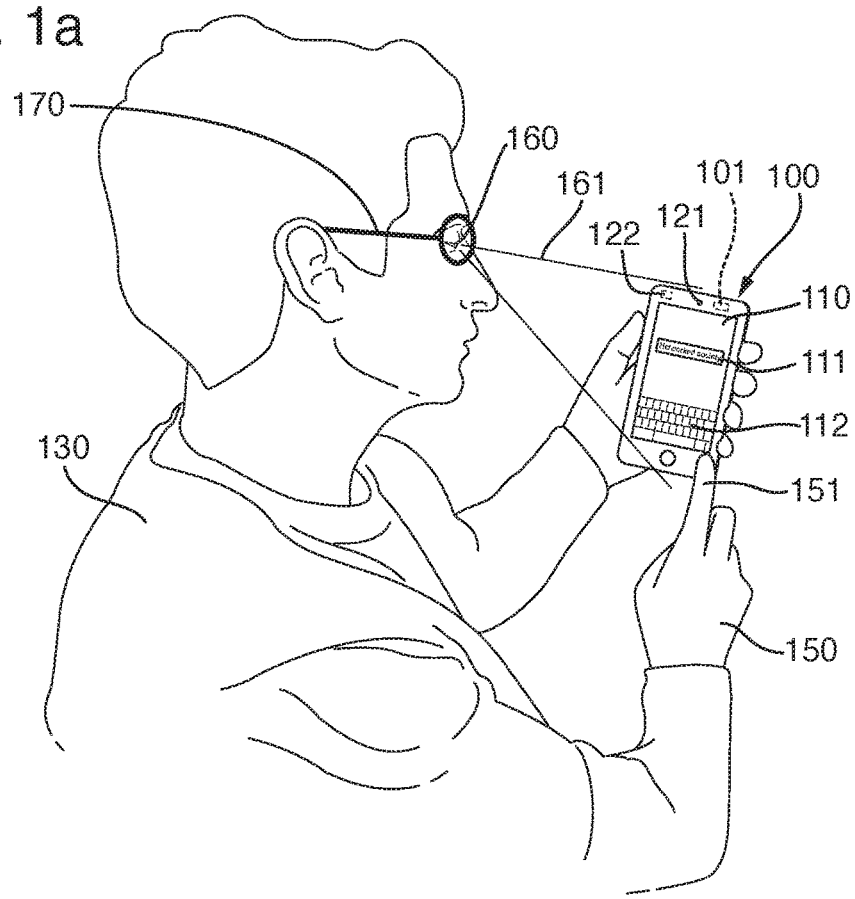
FIGS. 1a and 1b illustrate a device for corneal imaging, in accordance with an embodiment of the invention.

In FIG. 1a, a device 100 is shown, in accordance with an embodiment of the invention. Device 100, in FIG. 1a illustrated as a smartphone, comprises processing means 101, a screen 110, and a first camera 121. Screen 110 is operable as output device for device 100, i.e., for displaying graphical content such as user-interface elements, e.g., pictures, pieces of text, fields for entering or editing text (such as a text field 111), Uniform Resource Locators (URLs) or other links, virtual buttons or keys (such as a virtual keyboard 112), and the like. Screen 110 and the graphical objects displayed on it are controlled by processing means 101, e.g., an operating system or application being executed on processing means 101. Screen 110 may be a conventional screen of non-touchscreen type or a touchscreen, as is known in the art. Device 100 is illustrated as being operated by a user 130 and may be any type of computing device suitable for corneal imaging, such as a mobile phone, smartphone, tablet, laptop, or the like.

Throughout this disclosure, a user of a device is understood to be a person located so as to be able to operate the device, e.g., holding the device, sitting in front of a table on which the device is placed, or sitting next to a person holding the device. It is further to be understood that the user can control the device and/or enter information, e.g., by touching user-interface elements displayed on a touchscreen of the device.

First camera 121 has a field of view which is directed into the same direction as the viewing direction of screen 110. First camera 121 and screen 110 are preferably provided on the same face of device 100, i.e., camera 121 is a front-facing camera. Optionally, device 100 may comprise multiple front-facing cameras and also a rear-facing camera 122 on a face of device 100 which is opposite to the face on which screen 110 and camera 121 are provided.

Front-facing camera 121 is configured for imaging a cornea 162 of an eye 160 of user 130 of device 100 and/or an eyewear 170 worn by user 130, in FIG. 1a illustrated as glasses 170. In general, eyewear consists of items and accessories worn on or over the eyes, for fashion or adornment, protection against the environment, and to improve or enhance visual acuity. In the present context, eyewear may include common forms of eyewear such as glasses, also called eyeglasses or spectacles, sunglasses, and contact lenses, and more utilitarian forms of eye protection such as goggles.

Figure 1B:
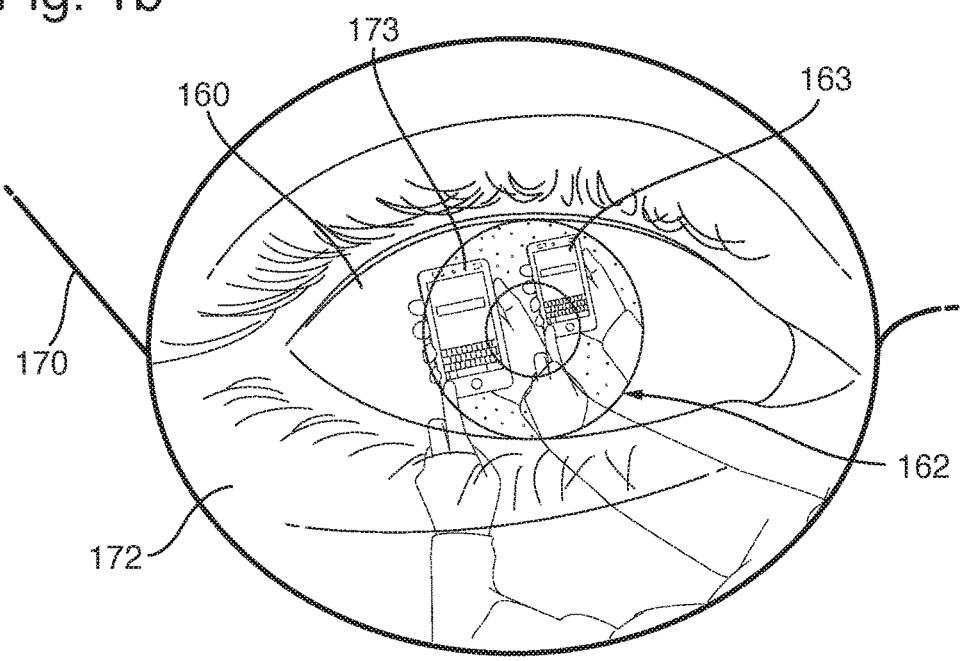

With reference to FIG. 1b, showing an enlarged view of eye 160 of user 130 and eyewear 170 worn by user 130, processing means 101 of device 100 is operative to acquire a first image from front-facing camera 121, identify a first reflection 163 by cornea 162 and, additionally or alternatively, a second reflection 173 by a reflective surface 172 of eyewear 170. First reflection 163 and/or second reflection 173 are identified by analyzing the first image, i.e., by image processing, as is known in the art.

An image processing algorithm for separating first reflection 163 and second reflection 173 may, e.g., be based on the parallax effect. As cornea 162 and lens 172 are at different distance from front-facing camera 121, any lateral motion will result in a larger displacement for second reflection 173, because lens 172 is presumably closer to front-facing camera 121, as compared to first reflection 163, since cornea 162 is presumably further away from front-facing camera 121. By tracking the motion of objects, e.g., full objects, partial objects, or sections of color, as the relative lateral position of first camera 121 and cornea 162 or lens 172 shifts, those objects can be determined to belong to first either reflection 163 or second refection 173. It will be appreciated that the lateral shift in relative position may be due to a natural movement of user 130's hand and/or head, or induced by displaying visual stimuli on screen 110, modifying graphical content displayed on screen 110, or by means of a haptic cue inducing user 130 to move and/or rotate device 100. Such a shift in relative position may also utilized for capturing multiple images of lens 172 and subsequently combining these multiple images into a 3D image, from which a geometrical model or the curvature of lens 172 may be derived.

A shift of first reflection 163 and/or second reflection 173 in the first image may also be detected by means of Eulerian video magnification, as described by H. Wu, M. Rubinstein, E. Shih, J. Guttag, F. Durand, and W. T. Freeman, "Eulerian Video Magnification for Revealing Subtle Changes in the World", in ACM Transactions on Graphics (Proc. SIGGRAPH 2012), 2012, vol. 31.

Further, in case front-facing camera 121 is capable of focusing the first image post capture, the first image may be adjusted such that first reflection 163 and second reflection 173 may be in focus at separate times, thereby facilitating separately identifying first reflection 163 and second reflection 173 in the first image.

With respect to first reflection 163, originating from cornea 162 of user 130, it is noted that light is mostly reflected by the cornea of the human eye, and that it is easier to detect reflections in the dark region of the iris as compared to the white sclera surrounding the iris. The technique of corneal imaging is made possible by the spherical nature of the human eyeball allowing gathering information about objects in a field of view 161 which may be wider than user 130's viewing field-of-view. Corneal imaging may, e.g., be used for capturing images of user 130's surroundings or for providing a touch-based user interface which utilizes front-facing camera 121 for capturing a top-down view of device 100, and in particular finger 151 touching screen 110 and the displayed user-interface elements. By analyzing an image capturing reflections of device 100 and finger 151, information about an interaction by user 130, using his/her finger 151, with device 100 can be inferred. For instance, device 100 may be configured for predicting which user-interface element displayed on screen 110 which user 130 intended to touch with finger 151, in addition to, or instead of, detecting a location of touch by touchscreen 110, as is known in the art.

User-interfaces and other solutions which are based on corneal imaging may suffer from specular reflections which originate from eyewear 170 worn by user 130. Second reflection 173, which is illustrated in FIG. 1b, may originate from a reflecting surface of eyewear 170, e.g., an outer surface of a lens 172 of glasses 170 or that of a contact lens. In general, multiple reflections may arise from eyewear 170, e.g., from the two surfaces of lens 172. For the sake of simplicity it is assumed here that only one of these multiple reflections is prominent in the first image acquired from camera 121. The number of reflections from eyewear 170 which are prominent in the first image may also depend on the type of eyewear and any surface coating applied to the eyewear, such as reflective coatings which are popular with sunglasses, or anti-reflective coatings which frequently are applied to lenses used for enhancing visual acuity.

It will also be appreciated that only one of the first reflection 163 and the second reflection 173 may be prominent in the first image. For instance, if lens 172 is provided with an anti-reflective coating, only first reflection 163 may be prominent in the first image, whereas only second reflection 173 may be prominent in the first image if lens 172 is provided with a highly reflective coating.

Processing means 101 is further operative to determine a first optical transformation representing first reflection 163, and, additionally or alternatively, a second optical transformation representing second reflection 173. In the present context, an optical transformation is to be understood as the transformation which describes the mapping of the environment, e.g., one or more objects in the surrounding of user 130, into the image plane of first camera 121. This mapping depends on the geometry of the reflecting surface, cornea 162 or a reflective surface 172 of eyewear 170, respectively, and its pose relative to first camera 121. Such an optical transformation may be expressed in mathematical terms, e.g., using a matrix notation. For instance, if P represents an undistorted image captured by first camera 121, i.e., an image of the surrounding of user 130 which has undergone reflection by a fictitious planar reflective surface at the location of cornea 162, the distortion imposed on P upon reflection by cornea 162 rather than the fictitious planar reflective surface can be described by a matrix $T_1$, the first optical transformation, such that $$P'_1 = T_1 \cdot P \qquad (1),$$

where $P'_1$ represents an image of first reflection 163.

Correspondingly, the second optical transformation $T_2$ may be defined as $$P'_2 = T_2 \cdot P \qquad (2),$$

where $P'_2$ represents an image of second reflection 173 as captured by first camera 121. $T_2$ describes the distortion imposed on P upon reflection by lens 172 rather than the fictitious planar reflective surface which has undergone reflection by a fictitious planar reflective surface at the location of lens 172.

In general, the first image captured by first camera 121 may comprise both reflections $P'_1$ and $P'_2$, but one of the reflections may be more prominent depending on the reflective properties of reflecting surface 172 of eyewear 170. Note that, owing to the field-of-view of first camera 121, first reflection 163 and second reflection 173, as represented by $P'_1$ and $P'_2$, respectively, typically only constitute a small portion of the first image.

The first image captured by first camera 121 is typically a bitmap or pixmap, i.e., a two-dimensional array of pixels carrying intensity and/or color information. Accordingly, each of first reflection 163 and second reflection 173, as represented by $P'_1$ and $P'_2$, respectively, constitute a section of bitmap or pixmap representing the first image. These sections may be identified by image processing the first image, as is known in the art. For instance, first reflection 163 and/or second reflection 173 may be identified in the first image by first identifying a face of user 130, and subsequently identifying eyewear 170 worn by user 130 and/or eye 160 or cornea 162 of user 130. The identified first reflection 163 and/or second reflection 173 may optionally be extracted from the first image, e.g., by cropping the first image, for further processing.

Processing means 101 is further operative to determine information which describes the first optical transformation and/or the second optical transformation. The information may, e.g., comprise matrices $T_1$ and/or $T_2$, respectively, describing the distortion imposed by reflection off cornea 162 or reflective surface 172, rather than a fictitious planar reflective surface. Alternatively, the information describing the first and/or second optical transformation may also describe the geometry of cornea 162 and/or reflective surface 172. Such information may, e.g., be derived based on the first and second optical transformations, as represented by matrices $T_1$ and $T_2$. For instance, the information describing the first optical transformation and/or the second optical transformation may comprise a first curvature of the cornea and/or a second curvature of a reflective surface of the eyewear. Optionally, the information may additionally comprise an eccentricity, if the reflective surface of the cornea or the eyewear can be approximated by an ellipsoid. As yet a further alternative, the information may be based on a matrix notation describing the geometry of the reflection surface of cornea 162 or reflective surface 172.

In the following, solutions for determining the first optical transformation and/or the second optical transformation are described, in accordance with embodiments of the invention.

For instance, embodiments of the invention may use a universal optical transformation representing reflection by the human cornea as the first optical transformation $T_1$, representing reflection by cornea 162. The first optical transformation may subsequently be used for determining the second optical transformation $T_2$, representing reflection by reflective surface 172 of eyewear 170, as is described further below. Using the universal optical transformation is advantageous in resource usage associated with image processing is reduced. It is based on the understanding that the adult human cornea can be modeled by an ellipsoid with parameters which do not vary much across people. Information describing the universal optical transformation may be based on a matrix notation, corresponding to $T_1$ as defined by Eq. (1), or may comprise parameters describing an ellipsoid which is used to approximate the adult human cornea, such as radius, curvature, eccentricity, or the like.

According to an embodiment of the invention, processing means 101 may further be operative to retrieve the information describing the second optical transformation $T_2$ from a database based on an identification of the eyewear. The database may either be provided in device 100 or accessible by device 100 through a communications network. For instance, device 100 may be configured for accessing the database through a Radio Access Network (RAN), such as a cellular mobile network or a Wireless Local Area Network (WLAN) as is described further below with reference to FIGS. 3 and 5, and the Internet. The information describing the second optical transformation is obtained by querying the database, i.e., by sending a request comprising information identifying the make and model of the eyewear 170. This may, e.g., be achieved by identifying the make and model of eyewear by imagine processing the first image and transmitting the make and model with the request. Alternatively, the first image, or a cropped part of the first image capturing eyewear 170 or at least characteristic features of eyewear 170, may be transmitted with the request. Optionally, the first image or the cropped part of the first image may be processed before transmitting the request, e.g., in order to reduce the size of the image. The second optical transformation may subsequently be used for determining the first optical transformation $T_1$, representing reflection by cornea 162, as is described further below.

As yet a further alternative, processing means 101 may be operative to determine the first optical transformation or the second optical transformation, or both, by identifying a reflection of device 100 in first reflection 163 or second reflection 173, as represented by $P_1'$ and $P_2'$, respectively, and determining the first optical transformation $T_1$ and/or the second optical transformation $T_2$ based on a shape of device 100. This is advantageous in that either one of the optical transformations $T_1$ and $T_2$ may be determined independently of each either, and without relying on identifying the eyewear and querying information from a database, or relying on a universal optical transformation for the human cornea. To this end, processing means is operative to identify device 100, or any characteristic features of device 100, such as its screen 110, and determine the first and/or the second optical transformation based on first 163 and/or second reflection 173 captured in the first image and the known shape of device 100 or screen 110. Utilizing screen 110 is particularly advantageous since it is typically has a rectangular area which is clearly visible in the first image.

According to an embodiment of the invention, processing means 101 may be operative to determine one of the optical transformations, i.e., either the first optical transformation $T_1$ or the second optical transformation $T_2$. Processing means 101 is further operative to identify at least one object which is visible in both first reflection 163 and second reflection 173, as represented by $P'_1$ and $P'_2$, and determining a third optical transformation $T_3$ between the at least one object in first reflection and the at least one object in second reflection 173, e.g., $$P'_2 = T_3 \cdot P'_1 \qquad (3).$$

Processing means 101 is further operative to determine the other optical transformation of the first optical transformation and the second optical transformation, i.e., the optical transformation which yet has to be determined, based on the already determined optical transformation and the third optical transformation.

For instance, if the first optical transformation $T_1$ is determined first, in accordance with one of the solutions described herein, e.g., using a universal optical transformation for the adult human cornea, the second optical transformation $T_2$ can be determined, since, combining Eqs. (2) and (3), $$P'_2 = T_3 \cdot T_1 \cdot P \qquad (4),$$

it follows that $$T_2 = T_3 \cdot T_1 \qquad (5).$$

Correspondingly, if the second optical transformation $T_2$ is determined first, e.g., by retrieving information describing the second optical transformation from a database, the first optical transformation $T_1$ can be determined as $$T_1 = T_3^{-1} \cdot T_2 \qquad (6),$$

where $T_3^{-1}$ is the inverse transformation of $T_3$.

Thus, if one of the optical transformations is known, the other optical transformation may be established based on one or more objects which are captured in both first reflection 163 and second reflection 173.

In the following, a further embodiment of device 100 is described with reference to FIG. 2a, illustrating a side-view.

In addition to what has been described hereinbefore, device 100 may further comprise a second camera 122 having a field-of-view 124 which is substantially opposite to a field-of-view 122 of first camera 121, commonly referred to as rear-facing camera. Further, processing means 101 is operative to determine the first optical transformation $T_1$ or the second optical transformation $T_2$, or both, by acquiring a second image from second camera 122 and identifying at least one object 201 (in FIG. 2a illustrated as a painting on a wall in front of user 130; for the sake of clarity painting 201 is not shown in perspective view) which is present in both the first image 210 and the second image 220. This is illustrated in FIG. 2b, which shows first image 210, captured by front-facing camera 121, containing a distorted reflection 211 of object 201, owing to reflection by cornea 162 or reflective surface 172, and second image 220, captured by rear-facing camera 122, presenting an undistorted image 221 of object 201. Note that reflection 211 may either be first reflection 163 or second reflection 173, depending on whether the first optical transformation $T_1$ or the second optical transformation $T_2$ is determined.

Processing means 101 is further operative to determine a fourth optical transformation $T_4$ between the at least one object in the first image (211 in FIG. 2b) and the at least one object in the second image (221 in FIG. 2b) and determine the first optical transformation $T_1$ and/or the second optical transformation $T_2$ based on the fourth optical transformation $T_4$. More specifically, if object 201 as presented in second image 220 is represented by $P'_4$ (221 in FIG. 2b), it follows that $$P'_4 = P \qquad (7),$$

since the image $P'_4$ 221 of object 201 captured by rear-facing camera 122 does not suffer from any distortion induced by reflection from a non-planar surface. Accordingly, the first optical transformation $T_1$ can be established, based on Eq. (1), from $$P'_1 = T_1 \cdot P'_4 \qquad (8).$$

Correspondingly, the second optical transformation $T_2$ can be established, based on Eq. (2), from $$P'_2 = T_2 \cdot P'_4 \qquad (9).$$

Determining the first and/or the second optical transformation by utilizing images captured by rear-facing camera 122 is advantageous in that these images do not suffer from distortion due to reflection from non-planar surfaces such as cornea 162 or reflective surface 172, e.g., a lens. In particular, the first optical transformation $T_1$ can be established as the optical transformation which transforms $P'_4$ into $P'_1$, and the second optical transformation $T_2$ can be established as the optical transformation which transforms $P'_4$ into $P'_2$. Note that the first optical transformation and the second optical transformation can be established independently of each other.

Optionally, processing means 101 may further be operative to provide the information describing the first optical transformation and/or the second optical transformation to an application being executed on device 100, e.g., on processing means 101. In particular, this may be an application utilizing corneal imaging. Thereby, the application may perform a corneal-imaging based task which it implements in an improved fashion. For example, an application for capturing images of user 130's environment utilizing corneal imaging may use the information describing the first optical transformation and/or the second optical transformation for processing the first image acquired by front-facing camera 121 so as to correct the distortion imposed by reflection off cornea 162 or reflective surface 172, resulting in an improved image.

Methods for correcting the distortion imposed by reflection off cornea 162, i.e., for reconstructing a scene captured by means of corneal imaging, are described in K. Nishino and S. K. Nayar, "Corneal Imaging System: Environment from the Eyes", in International Journal of Computer Vision, 2006, vol. 70, pages 23-40, and C. Nitschke, A. Nakazawa, and H. Takemura, "Corneal Imaging Revisited: An Overview of Corneal Reflection Analysis and Applications", in IPSJ Transactions on Computer Vision and Applications, 2013, vol. 5, pages 1-18. It will be appreciated that such methods may also be applied, with corresponding modifications, for correcting the distortion imposed by reflection off lens 172.

Optionally, processing means 101 may further be operative to provide an image of first reflection 163, i.e., an image containing $P'_1$, and/or an image of second reflection 173, i.e., and image containing $P'_2$. For instance, the application may generate a corrected image of first reflection 163 and/or second reflection 173 based on an image of first reflection 163 and/or an image of second reflection 173, in combination with the information describing the first optical transformation and/or the second optical transformation. The application may, e.g., be an application for capturing images of user 130's environment utilizing corneal imaging. It will also be appreciated that processing means 101 may further be operative to correct the image of first reflection 163, i.e., an image containing $P'_1$, and/or the image of second reflection 173, $P'_2$, based on the first optical transformation $T_1$ and/or the second optical transformation $T_2$, respectively. Thus, rather than providing images of user 130's environment which at least partly are distorted by reflection from a non-planar surface, such as cornea 162 or reflective surface 172, an embodiment of device 100 may be operative to correct the images of reflections 163 and 173 based on Eqs. (1) and (2), resulting in corrected images representing P. More specifically, the corrected image of first reflection 163 may be obtained as $$P_1 = T_1^{-1} \cdot P'_1 \qquad (10),$$

and the corrected image of the second reflection 173 may correspondingly be obtained as $$P_2 = T_2^{-1} \cdot P'_2 \qquad (11).$$

Note that if both first reflection 163 and second reflection 173 are captured in the first image, a corrected image may be derived for each of them. The two corrected images, $P_1$ and $P_2$, may differ, e.g., in quality, but also with respect to which part of user 130's environment they capture, owing to the different field-of-view of the combination of first camera 121 and cornea 162 (i.e., $P'_1$), as well as first camera 121 and reflective surface 172 (i.e., $P'_2$), respectively.

Further optionally, processing means 101 may be operative to provide a combined image of first reflection 163 and of second reflection 173. This may be achieved by first correcting the captured images of first reflection 163 and second reflection 173, $P'_1$ and $P'_2$, and subsequently combining, or overlaying, the corrected images $P_1$ and $P_2$. Advantageously, the combined image may be of superior quality than the two corrected images $P_1$ and $P_2$.

Processing means 101 may optionally be further operative to determine, for each of the image of the first reflection and the image of the second reflection, one or more metrics associated with requirements on an image of a reflection. The determination may either be performed for the captured images $P'_1$ and $P'_2$, or for the corrected images $P_1$ and $P_2$. The metrics may relate to any one of an image quality, an image resolution, a visibility of a certain object in the image, such as screen 110, and so forth. Processing means 101 is further operative to select an image for further use or processing based on the determined metrics or a combination of the determined metrics. For instance, an embodiment of device 100 may be operative to select the image from captured images $P'_1$ and $P'_2$ which is most suitable for establishing one of the optical transformations $T_1$ and $T_2$ based on the known shape of device 100 or screen 110, as was described above.

Optionally, processing means 101 may be operative to provide one or more of the images described hereinbefore, i.e., one or more of $P_1$, $P_2$, $P'_1$, $P'_2$, and a combined image, to an application being executed on the device, and in particular a corneal-imaging based application.

An embodiment of device 100, comprising screen 110 which is operable as output device for device 100, processing means 101 may further be operative to display graphical content on screen 110 so as to make user 130 move device 100 in relation to a head of user 130. This may, e.g., be achieved by decreasing a size of the displayed graphical content or by displaying blurred graphical content, such that user 130 is forced to move device 100 closer to his/her eye 160. This is advantageous in that images captured by front-facing camera 121 may be improved, e.g., in response to determining that one or more of the determined metrics associated with requirements on an image of a reflection do not fulfill requirements imposed by a cornea-imaging application. For instance, if an image of a reflection of device 100 or screen 110 is required for establishing the first and/or the second optical transformation, a requirement on the first image captured by front-facing camera 121 may relate to the presence or visibility of device 100 or screen 110 on the first image. If it is determined that such a requirement is not fulfilled by a captured first image, i.e., device 100 or screen 110 are not visible, graphical content may be displayed on screen 110 so as to make user 130 move device 100 so as to improve the visibility of device 100 or screen 110 in a reflection captured by front-facing camera 121.

Figure 3:
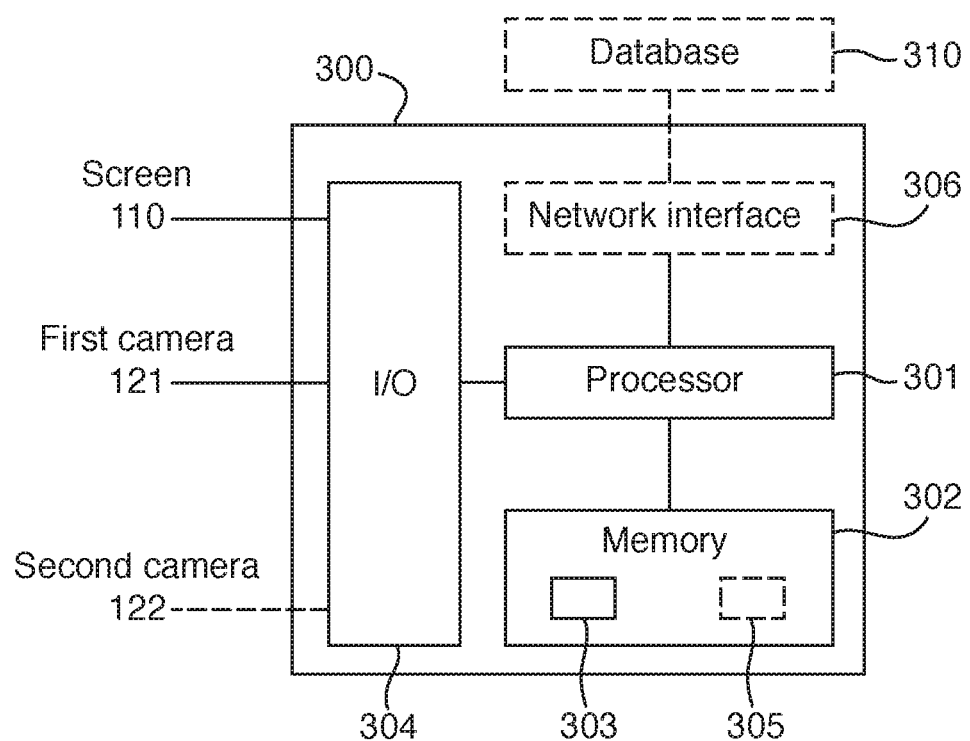
FIG. 3 shows a processing unit of a device for corneal imaging, in accordance with an embodiment of the invention.

In the following, an embodiment 300 of processing means 101 is described with reference to FIG. 3. Processing means 300 comprises a processor 301, e.g., a general purpose processor or a Digital Signal Processor (DPS), a memory 302 containing instructions, i.e., a computer program 303, and one or more interfaces 304 ("I/O" in FIG. 3) for receiving information from, and controlling, screen 110, first (front-facing) camera 121, and optional second (rear-facing) camera 122. Computer program 303 is executable by processor 301, whereby device 100 is operative to perform in accordance with embodiments of the invention, as described hereinbefore with reference to FIGS. 1 and 2. Processing means 300 may further comprise a network interface 306 which is operative for accessing a database 310 storing information describing the second optical transformation for different types, makes, and models, of eyewear. Processing means 300 may retrieve the information describing the second optical transformation for a specific eyewear, such as eyewear 170 illustrated in FIGS. 1 and 2, by sending a request comprising information identifying the eyewear, such as a make and model of the eyewear, or a section of an image acquired from first camera 121 and which captures the eyewear, to database 310. Alternatively, rather than retrieving information describing the second optical transformation for a specific eyewear from external database 310, embodiments of the invention may retrieve such information from a local database which device 100 is provided with, e.g., a database 305 stored in memory 302.

Figure 4:
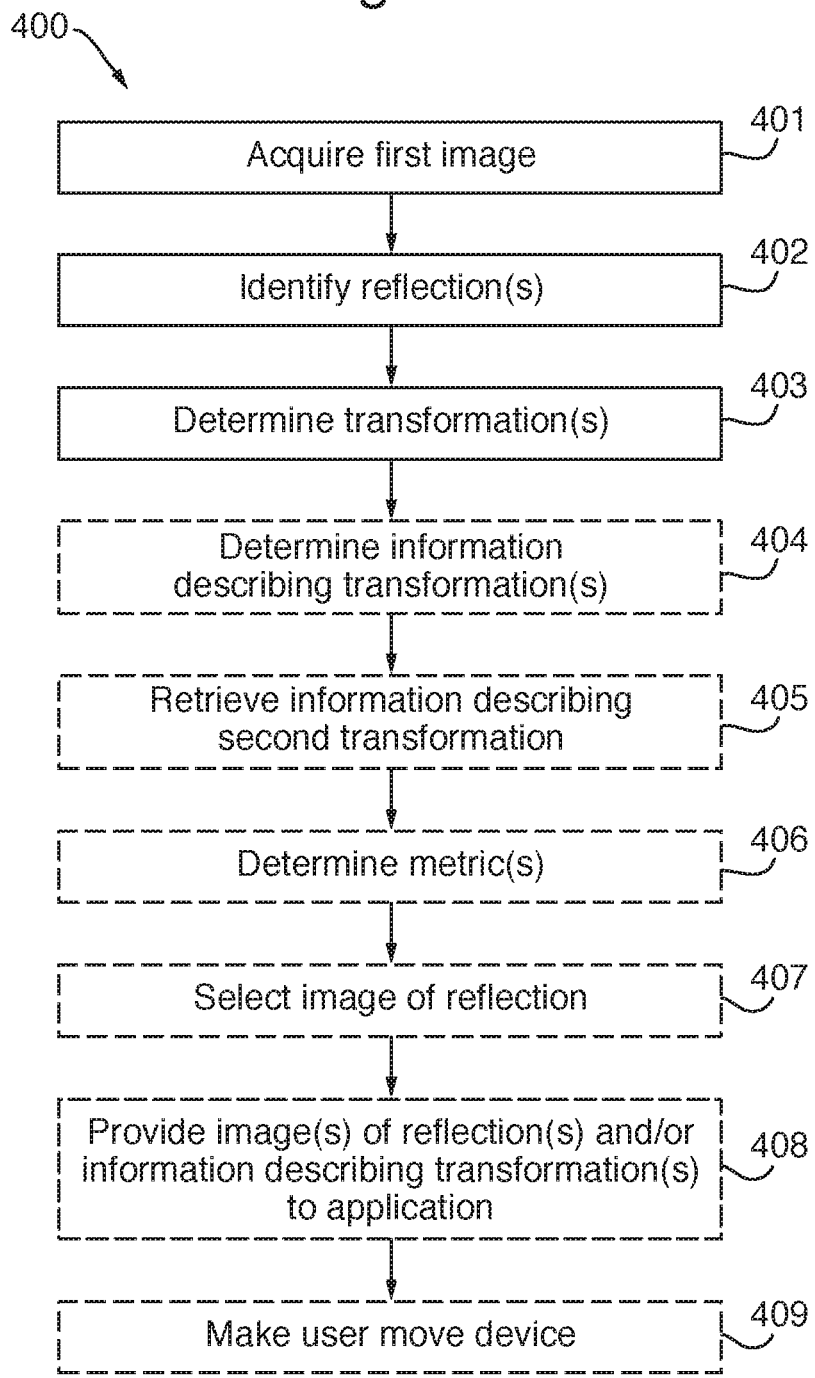
FIG. 4 shows a method of corneal imaging, in accordance with an embodiment of the invention.

In FIG. 4, a flowchart illustrating an embodiment 400 of the method of corneal imaging performed by a device, such as a mobile phone, a smartphone, a tablet, a laptop, or the like, is shown. Method 400 comprises acquiring 401 a first image from a first camera configured for imaging a cornea of a user of the device, an eyewear worn by the user, or both, and identifying 402 a first reflection by the cornea, a second reflection by a reflective surface of the eyewear, or both. The eyewear may, e.g., be glasses, spectacles, sunglasses, goggles, or a contact lens. The first reflection and/or the second reflection is/are identified by analyzing the first image, i.e., by image processing. Method 400 further comprises determining 403 a first optical transformation representing the first reflection, a second optical transformation representing the second reflection, or both, as is described hereinbefore with reference to FIGS. 1 and 2.

For instance, determining 403 the first optical transformation and/or the second optical transformation may comprise identifying a reflection of the device in the first reflection and/or the second reflection, and determining the first optical transformation and/or the second optical transformation based on a shape of the device. The reflection of the device may, e.g., be a reflection of a screen of the device.

As a further example, determining 403 the first optical transformation and/or the second optical transformation may comprise determining one of the first optical transformation and the second optical transformation, identifying at least one object which is visible in both the first reflection and the second reflection, determining a third optical transformation between the at least one object in the first reflection and the at least one object in the second reflection, and determining the other optical transformation of the first optical transformation and the second optical transformation based on the determined optical transformation and the third optical transformation.

As yet a further example, determining 403 the first optical transformation and/or the second optical transformation may comprise acquiring a second image from a second camera having a field-of-view which is substantially opposite to a field-of-view of the first camera, identifying at least one object which is present in both the first image and the second image, determining a fourth optical transformation between the at least one object in the first image and the at least one object in the second image, and determining the first optical transformation and/or the second optical transformation based on the fourth optical transformation.

Optionally, method 400 may further comprise determining 404 information describing the first optical transformation, the second optical transformation, or both. For instance, the information describing the second optical transformation may be retrieved 405 from a database, based on an identification of the eyewear.

Optionally, method 400 may further comprise determining 406, for each of the image of the first reflection and the image of the second reflection, one or more metrics associated with requirements on an image of a reflection, and selecting 407 an image of the image of the first reflection and the image of the second reflection based on the determined one or more metrics.

Optionally, method 400 may further comprise providing 408 the information describing the first optical transformation and/or the second optical transformation, or one or more images of the first reflection and/or the second reflection, to an application being executed on the device. The image of the first reflection and/or the image of the second reflection may optionally be corrected, based on the first optical transformation and/or the second optical transformation, respectively, and optionally be combined.

Optionally, method 400 may further comprise displaying 409 graphical content on a screen operable as output device for the device so as to make the user move the device in relation to a head of the user.

It will be appreciated that method 400 may comprise additional or modified steps in accordance with what is described hereinbefore. An embodiment of method 400 may be implemented as software, such as computer program 303, to be executed by a processor comprised in the device (such as processor 301 described with reference to FIG. 3), whereby the device is operative to perform in accordance with embodiments of the invention.

Figure 5:
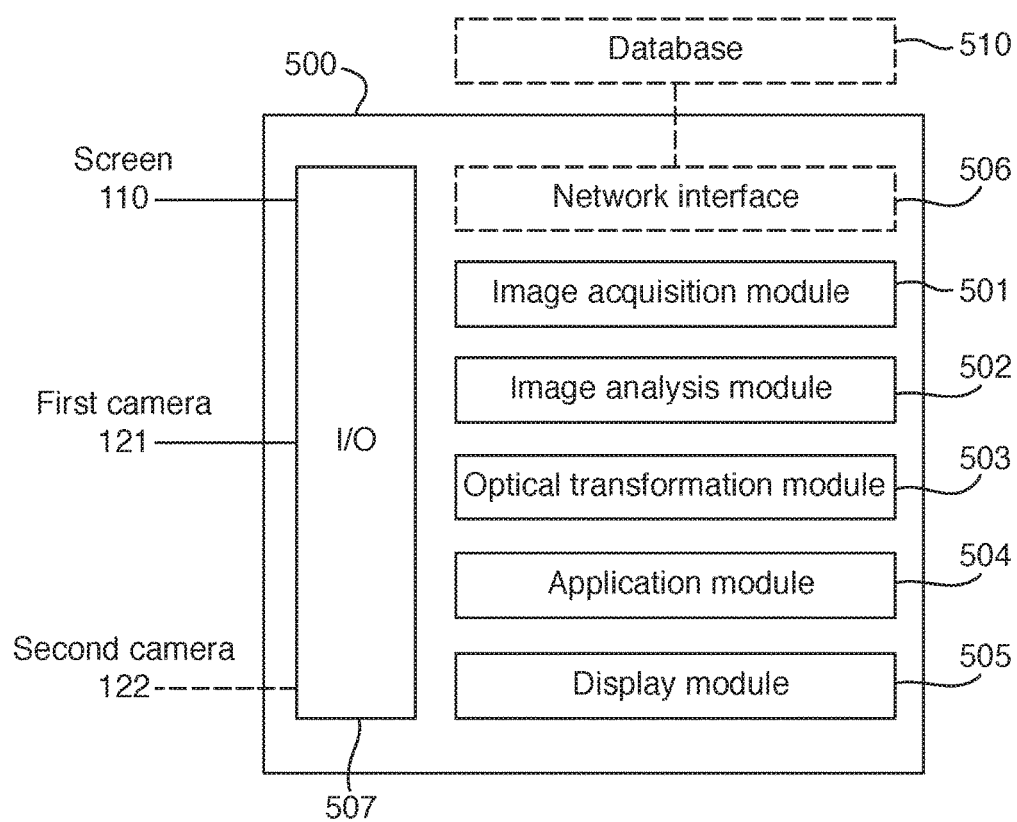
FIG. 5 shows a processing unit of a device for corneal imaging, in accordance with another embodiment of the invention.

In FIG. 5, an alternative embodiment 500 of processing means 101 is shown. Processing means 500 comprises one or more interface modules 507 ("I/O" in FIG. 7) for receiving information from, and controlling, screen 110, first (front-facing) camera 121, and optional second (rear-facing) camera 122. Processing means 500 further comprises an image acquisition module 501 configured for acquiring a first image from the first camera 121, an image analysis module 502 configured for identifying, by analyzing the first image, a first reflection by the cornea and/or a second reflection by a reflective surface of the eyewear, and an optical transformation module 503 configured for determining a first optical transformation representing the first reflection and/or a second optical transformation representing the second reflection.

Optical transformation module 503 may further be configured for determining information describing the first optical transformation and/or the second optical transformation.

Processing means 500 may further comprise a network interface 506 which is operative for accessing a database 510 storing information describing the second optical transformation for different types, makes, and models, of eyewear. Optical transformation module 503 may retrieve the information describing the second optical transformation for a specific eyewear, such as eyewear 170 illustrated in FIGS. 1 and 2, by sending a request comprising information identifying the eyewear, such as a make and model of the eyewear, or a section of an image acquired from first camera 121 and which captures the eyewear, to database 510. Alternatively, rather than retrieving information describing the second optical transformation for a specific eyewear from external database 510, embodiments of the invention may retrieve such information from a database module which device 100 is provided with (not shown in FIG. 5).

As an example, image analysis module 502 and optical transformation module 503 may be configured for determining the first optical transformation and/or the second optical transformation by identifying a reflection of the device in the first reflection and/or the second reflection, and determining the first optical transformation and/or the second optical transformation based on a shape of the device, respectively. The reflection of the device may be a reflection of the screen.

As a further example, image analysis module 502 and optical transformation module 503 may be configured for determining the first optical transformation and/or the second optical transformation by determining one of the first optical transformation and the second optical transformation, identifying at least one object which is visible in both the first reflection and the second reflection, determining a third optical transformation between the at least one object in the first reflection and the at least one object in the second reflection, and determining the other optical transformation of the first optical transformation and the second optical transformation based on the determined optical transformation and the third optical transformation.

As yet a further alternative, image analysis module 502 and optical transformation module 503 may be configured for determining the first optical transformation and/or the second optical transformation by acquiring a second image from the second camera, identifying at least one object which is present in both the first image and the second image, determining a fourth optical transformation between the at least one object in the first image and the at least one object in the second image, and determining the first optical transformation and/or the second optical transformation based on the fourth optical transformation.

Processing means 400 may further comprise an application module 504 configured for providing the information describing the first optical transformation and/or the second optical transformation, or one or more images of the first reflection and/or the second reflection, to an application being executed on the device. The image of the first reflection and/or the image of the second reflection may optionally be corrected, based on the first optical transformation and/or the second optical transformation, respectively, and optionally be combined Application module 504 may further be configured for determining, for each of the image of the first reflection and the image of the second reflection, one or more metrics associated with requirements on an image of a reflection, and selecting an image based on the determined one or more metrics.

Processing means 500 may further comprise a display module 505 configured for displaying graphical content on the screen so as to make the user move the device in relation to a head of the user.

It will be appreciated that modules 501-510, and any additional modules comprised in processing means 500, may be implemented by any kind of electronic circuitry, e.g., any one or a combination of analogue electronic circuitry, digital electronic circuitry, and processing means executing a suitable computer program.

The person skilled in the art realizes that the invention by no means is limited to the embodiments described above. On the contrary, many modifications and variations are possible within the scope of the appended claims.

The invention claimed is:

1. A device for corneal imaging, the device comprising:
    a camera configured for imaging, the camera outputting an image containing a first reflection from a cornea of a user of the device and a second reflection from a reflective surface of eyewear worn by the user;
    a processor connected to the camera; and
    a memory storing program instructions that are executed by the processor to perform operations comprising:
        acquiring the image from the camera;
        processing the image to identify at least one object in the first reflection from the cornea and in the second reflection from the reflective surface of the eyewear;
        determining one of a first optical transformation and a second optical transformation, based on the other one of the first optical transformation and the second optical transformation being previously determined and based on a third optical transformation comprising a mapping from the at least one object in the first reflection to the at least one object in the second reflection, wherein the first optical transformation comprises a first mapping from an undistorted image of the at least one object to the at least one object distorted in the first reflection in the image, and wherein the second optical transformation comprises a second mapping from an undistorted image of the at least one object to the at least one object distorted in the second reflection in the image;
        processing the image to generate a corrected image by correcting distortion in at least one of:
            at least a portion of the at least one object in the first reflection in the image based on the first optical transformation; and
            at least a portion of the at least one object in the second reflection in the image based on the second optical transformation; and
        providing the corrected image to an application.

2. The device according to claim 1, wherein the operations to determine one of the first optical transformation and the second optical transformation, comprises:
    obtaining from the memory the first optical transformation that is defined based on an approximation of an ellipsoid curvature for a human cornea;
    determining the second optical transformation representing the second reflection based on the first optical transformation obtained from the memory.

3. The device according to claim 2, wherein the first optical transformation is defined as a universal optical transformation representing distortion by the human cornea of objects shown in the first reflection contained in the image.

4. The device according to claim 1, wherein the operation to determine one of the first optical transformation and the second optical transformation, comprises:
    obtaining the second optical transformation based on curvature of the reflective surface of the eyewear that is determined from the second reflection;
    determining the first optical transformation representing the first reflection based on the second optical transformation.

5. The device according to claim 4, the operations further comprising:
    processing the image to identify a manufacturer and/or model of the eyewear; and
    obtaining the second optical transformation from a database using the identified manufacturer and/or model of the eyewear.

6. The device according to claim 5, the operations further comprising:
    generating a request message containing the identified manufacturer and/or model of the eyewear;
    communicating the request message through a network interface to a database via a radio access network; and
    receiving the second optical transformation from the database.

7. The device according to claim 5, wherein the database is a local database stored in the memory, and the operation to obtain the second optical transformation from the database using the identified manufacturer and/or model of the eyewear, comprises:
    querying the local database residing in the memory to obtain the second optical transformation.

8. The device according to claim 4, the operations further comprising:

generating a request message containing at least a portion of the image showing the eyewear;
communicating the request message through a network interface to a database via a radio access network; and
receiving the second optical transformation from the database.

9. The device according to claim 1, wherein the operation to determine one of the first optical transformation and the second optical transformation, comprises:
identifying a distorted shape of a part of a device that is shown in the first reflection and/or the second reflection; and
determining the first optical transformation and/or the second optical transformation based on a transformation determined between the distorted shape of the part of the device and a defined shape of the part of the device that is defined by data in the memory.

10. The device according to claim 9, wherein:
the operation to identify the distorted shape of the part of the device comprises identifying the distorted shape of a display screen of the device that is shown in the first reflection and/or the second reflection;
the operation to determine the first optical transformation and/or the second optical transformation is performed based on a transformation determined between the distorted shape of the display screen of the device and the defined shape of the display screen that is defined by the data in the memory.

11. The device according to claim 9, the operations further comprising:
determining that the operation to identify a distorted shape of the part of the device did not result in satisfying a defined requirement;
responsive to the determination that the defined requirement was not satisfied, displaying information on a display screen of the device to cause the user to move the device and/or the user's head relative to one another;
obtaining another image from the camera; and
repeating the processing of the other image to identify the first reflection from the cornea and the second reflection from the reflective surface of the eyewear and repeating the determining one of the first optical transformation representing the first reflection and the second optical transformation representing the second reflection, based on the other one of the first optical transformation and the second optical transformation.

12. The device according to claim 11, wherein the operation to display information on the display screen of the device to cause the user to move the device and/or the user's head relative to one another, comprises:
decreasing a size of graphical content displayed on the display screen and/or displaying blurred graphical content on the display screen to cause the user to change distance between the display screen and the cornea of the user.

13. The device according to claim 1 wherein providing the corrected image to the application comprises providing the corrected image to an application being executed by the device.

14. The device according to claim 1, wherein the operation to determine one of the first optical transformation and the second optical transformation, comprises:
identifying the at least one object which is visible in both the first reflection and the second reflection;
determining the third optical transformation.

15. A device for corneal imaging, the device comprising:
a first camera configured for imaging, the first camera outputting a first image containing a first reflection from a cornea of a user of the device and/or a second reflection from an eyewear worn by the user,
a second camera configured to have a field-of-view which is in a substantially opposite direction to a field-of-view of the first camera, and outputting a second image;
a processor connected to the first and second cameras; and
a memory storing program instructions that are executed by the processor to perform operations comprising:
acquiring the first image from the first camera;
processing the first image to identify the first reflection from the cornea and/or to identify the second reflection from the reflective surface of the eyewear;
acquiring the second image from the second camera;
processing the first and second images to identify an object which is present in both the first image and the second image;
determining a third optical transformation comprising a mapping from the object in the first image to the object in the second image;
determining at least one of a first optical transformation and a second optical transformation, based on the third optical transformation, wherein the first optical transformation comprises a first mapping from an undistorted image of the object to the object distorted in the first reflection in the first image, and wherein the second optical transformation comprises a second mapping from an undistorted image of the object to the object distorted in the second reflection in the first image;
processing the image to generate a corrected image by correcting distortion in at least one of:
at least a portion of the object in the first reflection in the image based on the first optical transformation; and
at least a portion of the object in the second reflection in the image based on the second optical transformation; and
providing the corrected image to an application.

16. The device according to claim 15, wherein providing the corrected image to the application comprises providing the corrected image to an application being executed by the device.

17. The device according to claim 15,
wherein the processing the first image to identify the first reflection from the cornea and/or to identify the second reflection from the reflective surface of the eyewear, comprises processing the first image to identify both the first reflection from the cornea and the second reflection from the reflective surface of the eyewear, and
the operations further comprising:
for each of the first reflection and the second reflection, determining a metric associated with the reflection, the metric indicating one of an image quality, an image resolution, a visibility of a certain object, and a presence of the certain object;
based on the metrics determined for the first and second reflections, controlling a selection between the first optical transformation and the second optical transformation that is determined based on the third optical transformation.

18. The device according to claim 15,
wherein the processing the first image to identify the first reflection from the cornea and/or to identify the second reflection from the reflective surface of the eyewear, comprises processing the first image to identify both the first reflection from the cornea and the second reflection from the reflective surface of the eyewear, and the operations further comprising:
for each of the first reflection and the second reflection, determining a metric associated with the reflection, the metric indicating one of an image quality, an image resolution, a visibility of a certain object, and a presence of the certain object;
based on the metrics determined for the first and second reflections, selecting one of the first reflection and the second reflection that is provided to a corneal imaging application.

19. The device according to claim 15, wherein the first optical transformation representing the first reflection and the second optical transformation representing the second reflection are both determined based on operations comprising:
obtaining from the memory the first optical transformation that is defined based on an approximation of an ellipsoid curvature for a human cornea; and
determining the second optical transformation representing the second reflection based on the first optical transformation obtained from the memory and based on the third optical transformation.

20. The device according to claim 19, wherein the first optical transformation is defined as a universal optical transformation representing distortion by the human cornea of objects shown in the first reflection contained in the image.

21. The device according to claim 15, wherein the first optical transformation representing the first reflection and the second optical transformation representing the second reflection are both determined based on operations comprising:
obtaining the second optical transformation based on curvature of the reflective surface of the eyewear that is determined from the second reflection; and
determining the first optical transformation representing the first reflection based on the second optical transformation and based on the third optical transformation.

22. The device according to claim 21, the operation to obtain the second optical transformation based on curvature of the reflective surface of the eyewear that is determined from the second reflection, comprises:
processing the first image to identify a manufacturer and/or model of the eyewear; and
obtaining the second optical transformation from a database using the identified manufacturer and/or model of the eyewear.

23. The device according to claim 22, the operation to obtain the second optical transformation from the database using the identified manufacturer and/or model of the eyewear, comprises:
generating a request message containing the identified manufacturer and/or model of the eyewear;
communicating the request message through a network interface to a database via a radio access network; and
receiving the second optical transformation from the database.

24. The device according to claim 22, wherein the database is a local database stored in the memory, and the operation to obtain the second optical transformation from the database using the identified manufacturer and/or model of the eyewear, comprises:

querying the local database residing in the memory to obtain the second optical transformation.

25. The device according to claim 21, the operation to obtain the second optical transformation based on curvature of the reflective surface of the eyewear that is determined from the second reflection, comprises:
generating a request message containing at least a portion of the first image showing the eyewear;
communicating the request message through a network interface to a database via a radio access network; and
receiving the second optical transformation from the database.

26. The device according to claim 15, wherein the operation to determine at least one of the first optical transformation representing the first reflection and the second optical transformation representing the second reflection, based on the third optical transformation, comprises:
identifying a distorted shape of a part of a device that is shown in the first reflection and/or the second reflection; and
determining the first optical transformation and/or the second optical transformation based on a fourth optical transformation determined between the distorted shape of the part of the device and a defined shape of the part of the device that is defined by data in the memory.

27. The device according to claim 26, wherein:
the operation to identify the distorted shape of the part of the device comprises identifying the distorted shape of a display screen of the device that is shown in the first reflection and/or the second reflection; and
the fourth optical transformation is determined between the distorted shape of the display screen of the device and the defined shape of the display screen that is defined by the data in the memory.

28. The device according to claim 26, the operations further comprising:
determining that the operation to identify a distorted shape of the part of the device did not result in satisfying a defined requirement;
responsive to the determination that the defined requirement was not satisfied, displaying information on a display screen of the device to cause the user to move the device and/or the user's head relative to one another;
acquiring another first image from the first camera;
processing the another first image to identify the first reflection from the cornea and/or to identify the second reflection from the reflective surface of the eyewear;
acquiring another second image from the second camera;
processing the another second image to identify an object which is present in both the another first image and the another second image;
determining another third optical transformation between the object in the another first image and the object in the another second image; and
determining at least one of the first optical transformation representing the first reflection and the second optical transformation representing the second reflection, based on the another third optical transformation.

29. The device according to claim 28, wherein the operation to display information on the display screen of the device to cause the user to move the device and/or the user's head relative to one another, comprises:
decreasing a size of graphical content displayed on the display screen and/or displaying blurred graphical content on the display screen to cause the user to change distance between the display screen and the cornea of the user.

30. The device according to claim 15, the operations further comprising:
processing the first image to correct distortion in at least a portion of the first reflection based on the first optical transformation and/or to correct distortion in at least a portion of the second reflection based on the second optical transformation, to generate a corrected image with the distortion corrected.

31. The device according to claim 30, the operations further comprising:
providing the corrected image to an application being executed by the device.

* * * * *